United States Patent [19]
Cohen

[11] 3,991,765
[45] Nov. 16, 1976

[54] CRICOTHYROTOMY APPARATUS

[76] Inventor: Howard Cohen, 2791 W. 5th St., Brooklyn, N.Y. 11224

[22] Filed: Apr. 9, 1975

[21] Appl. No.: 566,447

[52] U.S. Cl. ............................................. 128/305
[51] Int. Cl.² ................ A61B 17/24; A61B 17/32; A61M 16/00
[58] Field of Search ............................. 128/303, 305

[56] References Cited
UNITED STATES PATENTS

| | | | |
|---|---|---|---|
| 3,182,663 | 5/1965 | Abelson | 128/305 |
| 3,704,529 | 12/1972 | Cioppa | 128/305 X |
| 3,791,386 | 2/1974 | McDonald | 128/305 |

*Primary Examiner*—Channing L. Pace
*Attorney, Agent, or Firm*—Robert W. Fiddler

[57] ABSTRACT

Cricothyrotomy apparatus for establishing an emergency breathing path for patients experiencing upper respiratory obstruction. The apparatus here provided enables the user to perform the necessary operative steps on a patient in a relatively automatic and hidden fashion, so that the user is not aware of the fact that he is piercing the patient's throat and inserting a tube therein. This is accomplished by providing a housing enclosing a spring pressed surgical blade and spring pressed tube or according to a second embodiment, a combined spring pressed tube and blade. A release mechanism actuated by a simple pressure button on the exterior of the housing releases the knife and tube (or tube with piercing blade) for automatic positioning at the desired point in the throat of the patient. A location marker is further provided to insure desired positioning of the cut and tube on the patient.

16 Claims, 8 Drawing Figures

CRICOTHYROTOMY APPARATUS

BACKGROUND OF THE INVENTION

This invention relates to apparatus for providing an emergency breathing path for patients experiencing upper respiratory obstruction, and more particularly, to cricothyrotomy apparatus for establishing the desired emergency breathing path by inserting a breathing tube through the cricothyroid membrane of a patient by a user, who is generally unfamiliar with the necessary surgical techniques.

A variety of situations exist in which it is necessary to provide a patient with an emergency breathing path. Thus, asphyxiation often occurs due to the inadvertent blocking of the trachea or windpipe, such as may occur when food is improperly swallowed and becomes lodged in the trachea; or due to a laryngal spasm or constriction resulting from a variety of allergic reactions.

In the event of such laryngal or tracheal obstruction, it is necessary to quickly provide an alternative breathing path to the lungs, to prevent death or brain damage.

A variety of surgical apparatus, including a variety of tracheotomy or cricothyrotomy tubes, have been evolved which are inserted into the windpipe beneath the area of obstruction, to provide an alternative emergency breathing path for the patient. The insertion of such cricothyrotomy or tracheotomy tubes requires surgical skills, and is generally performed in hospitals, or by surgically skilled personnel brought to the site of the emergency.

Unfortunately, patients experiencing windpipe blockages are often not located where the necessary apparatus or surgically trained personnel are available, and many patients asphyxiate long before the necessary apparatus or personnel become available. Thus, a large number of people asphyxiate each year in restaurants and in the home, due to food lodging in the windpipe or laryngal spasms or constrictions resulting from allergic reactions.

The desirability of providing cricothyrotomy apparatus which may be used by lay personnel in treating patients asphyxiating due to a windpipe blockage has been recognized, as for example by Tarsitano in U.S. Pat. No. 3,476,113, in which a pocket-sized cricothyrotomy set is provided having in a single readily portable kit, a syringe and needle for providing a local anesthetic; a surgical knife for cutting the necessary opening in the throat; and a breathing tube for insertion into the throat opening. Problems, however, arise in the use of this kit, since it is necessary that the user have a relatively sophisticated knowledge of the procedure to be followed. Such user must be aware of the particular location where the cut is to be made, and must have the presence of mind and intestinal fortitude to first stick a needle into the throat and release the necessary anesthetic; and thereafter actually cut into the throat with the knife blade provided, with the subsequent insertion of the breathing tube. As is apparent, most people in their homes, and certainly in restaurants, or the like, do not have either the information or presence of mind sufficient to perform the necessary surgical functions.

Wolf, in U.S. Pat. No. 3,841,334, shows another form of cricothyrotomy kit in which a plurality of hollow needles are arranged in a holder adapted to be positioned against the neck of the wearer. Within the needles are a plurality of stilettes or thin surgical knives, which are forced through the tubes into the patient's throat, and thereafter the hollow needles are forced into the throat about the stilettes, to provide the necessary air passage. As with Tarsitano, the user must know precisely where to locate the holder and needles, and must have the intestinal fortitude to drive the stilettes and needles into the throat of the patient. As is apparent, the average lay person neither has the skill nor desire to utilize equipment of the type evolved by Wolf or Tarsitano.

BRIEF DESCRIPTION OF THE INVENTION

It is with the above problems and considerations in mind, that the present improved cricothyrotomy apparatus has been evolved for establishing an emergency breathing path in patients experiencing upper respiratory obstruction, with the apparatus subject to being used by the lay person, with little or no surgical skill or knowledge, with the throat cutting and tube inserting activities kept hidden from the user.

It is accordingly among the primary objects of this invention to provide cricothyrotomy apparatus which may be used in an emergency situation by a lay user having no surgical skill or knowledge to provide an emergency breathing path for patients experiencing upper respiratory obstruction.

A further object of the invention is to provide cricothyrotomy apparatus which may be located at the necessary point on the patient's throat by those having little or no surgical skill.

A further object of the invention is to provide cricothyrotomy apparatus in which the necessary throat cutting action is taken in a relatively automatic and hidden fashion, without the user being aware of the fact that he is performing a throat cutting operation.

It is also an object of the invention to provide improved cricothyrotomy apparatus in which a tube is inserted into the throat of a patient in a relatively automatic and hidden fashion by a user who is relatively unaware of the fact that he is inserting a tube into the throat of the patient.

Another important object of the invention is to provide a simple, compact cricothyrotomy apparatus which may readily be maintained in the home or most public places for quick use in emergency situations by the unskilled layman.

These and other objects of the invention which will become hereafter apparent are achieved by providing a cricothyrotomy apparatus comprising a notched marking strip in which the notch is arcuately contoured to correspond to the lower contour of the adam's apple. The marking strip may either be formed as a simple strip of adhesive tape notched with the adam's apple contour, or may be formed of sheet plastic, having an attaching strap extending about the neck of the wearer. The attaching strap may suitably be formed with securing means such as snaps or mating Velcro tabs, to adjustably secure the strap firmly about the neck of the wearer, with the marking strip held in place beneath the adam's apple. Guide elements on the marking strip extend upwardly therefrom. A hand holdable housing is provided containing a releasably retained spring pressed air tube substantially enclosed therein. According to one embodiment of the invention, a releasably retained surgical knife blade is also maintained in the housing. According to another embodiment of the invention, the air tube is formed with a piercing blade at its leading edge. A detent rod having detents releasably engaging the spring pressed tube and blade is arranged within the housing, with the detent rod subject to actuation by a button exposed on the housing surface to release, first the knife, then the tube.

In use, the marking strip is positioned about the neck of the wearer, with the notch of the strip arranged beneath the adam's apple. The housing with the spring pressed knife and tube retracted therein is positioned over the marking strip, and the button on the housing is pressed. According to one embodiment of the invention, pressing the button first releases the knife blade, which enters the throat of the patient through the cricothyroid membrane between the thyroid cartilage and cricoid cartilage. Further depression of the button on the housing releases the tube, which enters the throat through the slit made by the knife. According to another embodiment of the invention, the pressing of the button releases the tube with the piercing blade tip spring pressed into the throat. The user is unaware of this throat cutting action, since the blade and tube are hidden by the housing, and all that is observed by the user is the pressing of the button. Thereafter, the housing is removed, leaving only the flanged tube in the throat opening, providing the desired emergency air passage.

An important feature of the invention resides in the fact that the user is substantially unaware of the throat cutting action, thus eliminating any queasiness which would normally be encountered by the lay user, unfamiliar with surgical procedure.

Another feature of the invention resides in the fact that the positioning of the apparatus at the necessary location on the throat to provide the cut in the cricothyroid membrane requires no anatomical knowledge as a result of the positioning of the marking strip immediately beneath the adam's apple.

An additional feature of the invention resides in the fact that the apparatus may readily be stored ready for use, and when used, does not require any surgical skills.

Another feature of the invention resides in the provision of a flange in the housing, limiting the depth of penetration of the knife into the throat of the patient.

A further feature of the invention resides in the fact that the apparatus is such as to permit use to provide a cricothyrotomy in less than 90 seconds after an asphyxiating peson may become unconscious, thus minimizing the possibility of brain damage.

BRIEF DESCRIPTION OF THE DRAWINGS

The specific details of a preferred embodiment of the invention and their mode of functioning, and the best mode presently contemplated for carrying out the invention so as to enable those skilled in the art to make and use same, will be described in clear, concise, and exact terms in conjunction with the accompanying drawings, wherein.

DESCRIPTION OF PREFERRED EMBODIMENT

Figure 1:
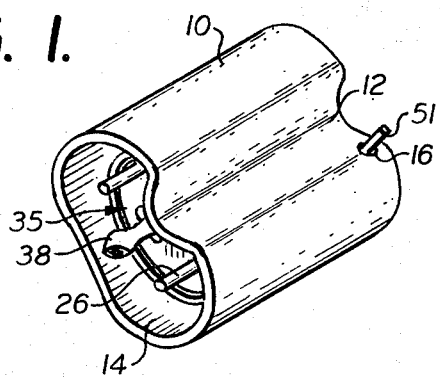
FIG. 1 is a perspective view of a cricothyrotomy apparatus made in accordance with the teachings of the invention employing a spring pressed knife blade and spring pressed tube showing the outer housing and the tube.

As seen in the drawings, where like parts are given like numbers, the inventive concept is illustratively shown as embodied in connection with a cricothyrotomy apparatus. Two embodiments are disclosed:

FIG. 1-5 EMBODIMENT

Figure 2:
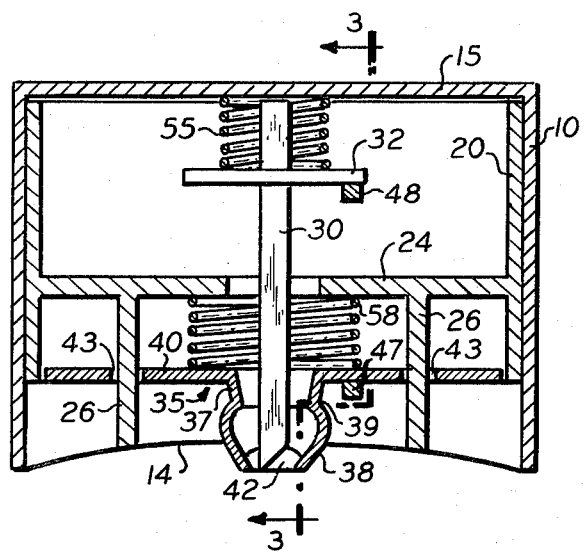
FIG. 2 is an enlarged cross-sectional view along the long axis of FIG. 1, showing the releasably retained spring pressed blade and spring pressed tube within the housing.
Figure 3:
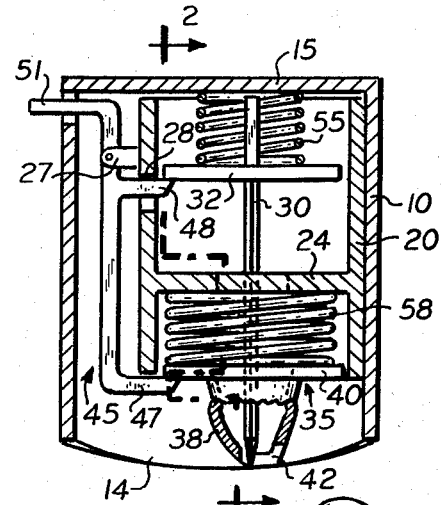
FIG. 3 is a cross-sectional view on line 3—3 of FIG. 2.
Figure 4:
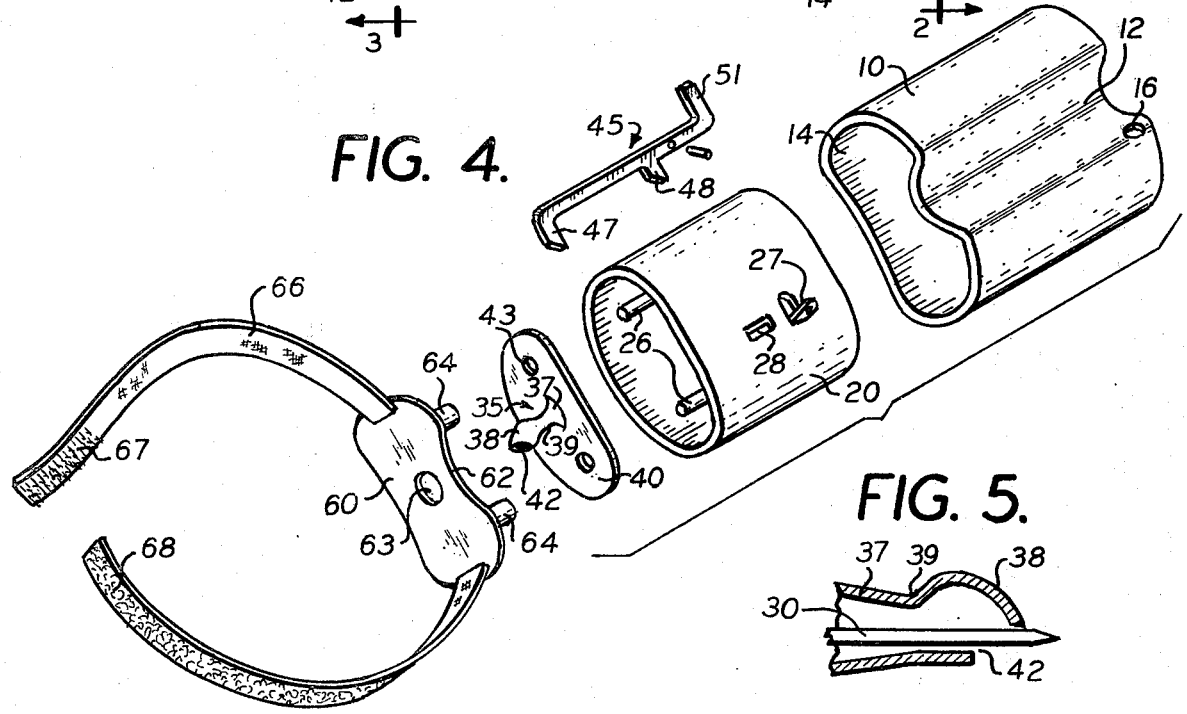
FIG. 4 is an exploded view of the FIG. 1-3 embodiment showing the components of the apparatus, along with the marking strip, here shown as provided with an attaching band.
Figure 5:
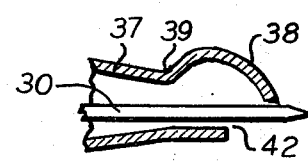
FIG. 5 is an enlarged cross-sectional detail view through the tip of air tube assembly of the FIG. 1-3 embodiment showing the contouring of the air tube.

In the FIG. 1-5 embodiment, the apparatus is shown as having housing 10, which, as best seen in FIGS. 1 and 4, is formed with an oval cross-section with a longitudinally extending indention 12. One end of the housing 10 is open, as at 14, and the other end is closed, as at 15, as best seen in FIGS. 2 and 3. The open end 14 of housing 10 is preferably arcuately contoured to fit against the throat of a patient. A button opening 16 is formed in the housing.

In the illustrated embodiments, the housing 10 is provided with an inner sleeve 20, as best seen in FIGS. 2, 3 and 4. Inner sleeve 20, like housing 10, is of an oval cross-section. However, though the major axis of the oval of the sleeve 20 is only slightly smaller than the major axis of the oval of the outer housing (so as to permit a slip fit into housing 10), the minor axis of the sleeve is dimensioned to slide between the housing indentation and the bottom housing wall to provide clearance between the sleeve 20 and outer housing 10, as best seen in FIG. 3. An annular flange 24, as best seen in FIGS. 2 and 3, extends inwardly from the inner sidewalls of the sleeve 20 to opening 25, and guide members, illustratively shown as rods 26, are preferably extended from the flange 24. Flange 24 provides a spring bearing surface and knife stop as will be hereafter apparent. The sleeve 20 is provided with a fulcrum 27, and detent opening 28, as best seen in FIG. 4.

A surgical knife blade 30 is arranged within sleeve 20, as best seen in FIGS. 2 and 3, with the knife freely slideable through flange opening 25. The surgical knife blade 30 is provided with a knife flange 32, dimensioned to overlap the flange 24 of sleeve 20, so that the knife is limited in its extension from the housing by knife flange 32 contacting annular flange 24.

An air tube assembly 35, having an air tube 37 contoured with a bulbous lower end 38 and constricted neck portion 39 transitioning into a flange portion 40 is provided. As illustratively shown, the air tube 37 is preferably provided with an outlet opening 42, arranged to face downwardly in the throat of the patient when inserted. Air tube flange 40 is formed with guide openings 43 of a dimension slightly larger than guide rods 26 to slide freely thereover, as best seen in FIG. 3, and the flange 40 is contoured of a dimension to slide freely in sleeve 20 and housing 10.

A detent rod 45, as best seen in FIGS. 3 and 4, is pivotally supported on fulcrum 27 on sleeve 20. The detent rod 45 is provided with a lower tube flange engaging detent 47, and a relatively shorter upper knife flange engaging detent 48. Lower detent 47 is of a dimension to extend beneath the lower edge of sleeve 20, as viewed in FIG. 3, into engagement with tube flange 40, and the upper detent 48, which is shorter than lower detent opening 28 into engagement with the knife flange 32. A detent lever actuating button 51 extends from the detent lever 45 through a button opening 16 in housing 10, as best seen in FIGS. 1 and 3.

Knife biasing spring 55 is arranged above knife flange 32, compressed between knife flange 32 and housing top 15, as best seen in FIGS. 2 and 3. Tube assembly biasing spring 58 is compressed between flange 24, and the top of tube flange 40, as best seen in FIGS. 2 and 3, with the springs 55 and 58 biasing the knife and tube towards the open housing end.

A location marking strip 60, as best seen in FIG. 4, is formed of sheet material, and contoured with an arcuate notch 62, shaped to conform to the bottom of a typical adam's apple. Marking strip 60 may be simply formed of a piece of adhesive tape marked with a center marking 63, identifying the point of incision which will coincide with the cricothyroid membrane. However, in accordance with the illustrated preferred embodiment, this marking strip is shown as formed of sheet plastic provided with central opening 63, dimensioned to freely pass the bulbous portion 38 of tube 35. Guide members in the form of hollow guide tubes 64, dimensioned to accommodate guide rods 26 extend up from marking strip 60 about the guide rods into guide openings 43 of tube flange 40. A strap 66 may, if desired, be employed to facilitate holding marking strip 60 in position on the neck of the patient. As illustratively shown, this strap 66 is provided with adjustable fastening means in the form of Velcro arranged with mating Velcro tabs 67 and 68 on the free ends of strap 66.

FIG. 6–8 EMBODIMENT

Figure 6:
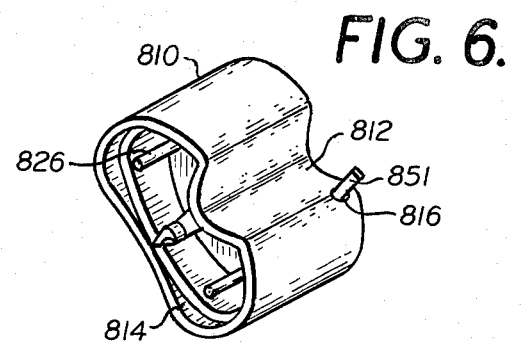
FIG. 6 is a perspective view of another embodiment of the cricothyrotomy apparatus employing a spring pressed tube with throat piercing blade entry tip, showing the outer housing and tube tip.
Figure 7:
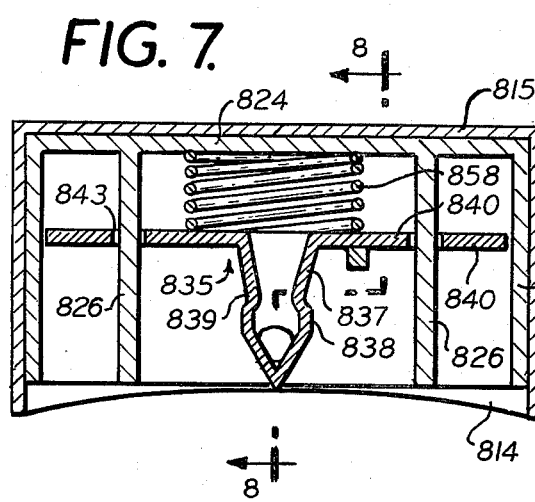
FIG. 7 is an enlarged cross-sectional view along the long axis of FIG. 6 showing the releasably retained spring pressed blade tipped tube in the housing.
Figure 8:
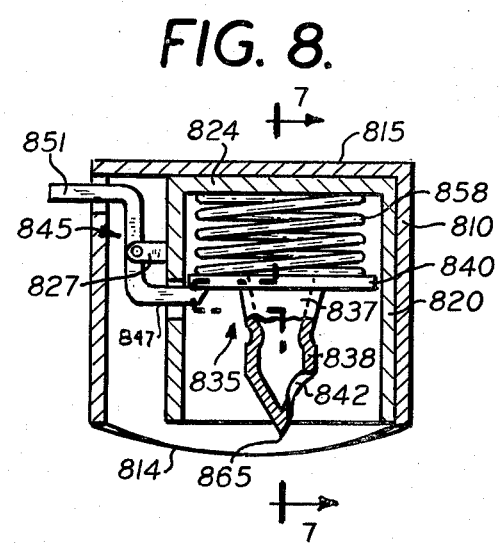
FIG. 8 is a cross-sectional view on line 8—8 of FIG. 7.

In the FIG. 6–8 embodiment, the separate spring pressed knife blade 30 of the FIG. 1–5 embodiment is substituted by forming a penetrating blade on the entry tip of the air tube. Parts of the FIG. 6–8 embodiment corresponding to those of the above described FIG. 1–5 embodiment will be numbered with numbers having the digit 8 prefixed to the number assigned the part of the FIG. 6–8 embodiment corresponding to the like parts of the FIG. 1–5 embodiment.

As in the FIG. 1–5 embodiment, the apparatus is formed with a housing 810, having an indent 812, an open lower end 814, a closed upper end 815 and detent button opening 816.

Sleeve 820, as best seen in FIGS. 7 and 8, fits in housing 810, with space for detent rod 845, with a spring housing flange 824 formed by the upper closed end of the sleeve 820. Guide rods 826 extend down from the flange 824, and a fulcrum 827, as best seen in FIG. 8, is formed on the side of the sleeve 820 between the sleeve and the housing 810.

The air tube assembly 835 has an air tube 837, bulbous lower end 838 and constricted neck portion 839, transistioning into flange 840. The lower end of the tube is formed with outlet opening 842 and flange 840 is formed with guide openings 843.

The bulbous lower end is formed with a penetrating entry tip blade 865 having the sharpness of a surgical blade serving to penetrate the throat of the patient as the tube is inserted.

A detent rod 845 having a tube flange engaging detent 847 is pivoted on fulcrum 827, as best seen in FIG. 8, and detent button 851 extends through opening 816 in housing 810.

Tube assembly biasing spring 858 is compressed between sleeve flange 824 and tube flange 840, with spring 848 exerting a biasing force urging the tube assembly towards the open housing end 814.

OPERATION

As is apparent to those skilled in the art, the FIG. 1–5 and FIG. 6–8 embodiments have a substantially similar mode of assembly and operation. In the following description, for purposes of brevity, where the description is applicable, both embodiments will be simultaneously described.

In assembling the FIG. 1–5 embodiment, knife spring 55 is arranged about the upper end of surgical knife blade 30, as viewed in FIGS. 2 and 3, and the blade is inserted into the housing 10 with the spring 55 compressed between knife flange 32 and housing top 15. Sleeve 20, which has had detent rod 45 pivotally attached to the fulcrum 27 is slid into housing 20 with the detent rod actuating button 51, extending through housing button opening 16. Tube assembly 35 is slid into sleeve 20, with tube biasing spring 58 sandwiched between annular sleeve flange 24 and tube flange 40, and detents 47 and 48 are positioned against the lower surface as viewed in FIGS. 2 and 3 of knife flange 32 and tube flange 40, to maintain the assembly in the position seen in FIGS. 2 and 3.

The FIG. 6–8 embodiment is similarly assembled by arranging the sleeve 820 with detent rod 845 in housing 810, and thereafter inserting the spring 858 and tube assembly 835 in the sleeve with detent 847 engaging beneath the tube plate 840 to retain the tube assembly against the biasing action of spring 857.

The assembled cricothyrotomy apparatus of the type shown in FIG. 1 or FIG. 6, along with the marking strip 60, is made available to the potential user.

In emergency situations, where a patient, such as a patient in a dental office, or a customer in a restaurant, experiences a throat blockage due to improper swallowing of food or an allergic reaction to food, or some other external stimulant resulting in a throat constriction interfering with normal breathing requiring the provision of an emergency air passage, the apparatus is employed by first positioning the marking strip 60 over the throat of the patient, with the notch 62 arranged beneath the adam's apple produced by the bulge of the thyroid cartilage. The center of the marking strip will thus lie at the cricothyroid ligament between the thyroid cartilage and the cricoid cartilage. The assembly (either FIG. 1 or FIG. 6) is then positioned over the marking strip, with guide rods 26 or 826 inserted in guide tubes 64 or 264. Thereafter, depression of button 51 or 851 will cause the detent rod 45 or 845 to pivot about fulcrum 27 or 827.

In the FIG. 1–5 embodiment, the shorter detent 48 releases knife flange 32, while longer detent 47 is still engaged with tube flange 40. Upon release of knife flange 32, spring 55 will bias the knife blade 30 into the throat of the patient to form a slit in the cricothyroid cartilage. Continued depression of button 51 results in release of tube flange 40 by detent 47, so that spring 58 will urge the tube assembly over the knife into the slit formed thereby.

In the FIG. 6–8 embodiment, the knife blade is formed at the entry tip of the tube, so that pressing button 851 pivots detent rod 845 to a position releasing tube assembly 840. Spring 858 then forces the tube against the patient's throat with knife blade tip 845 slitting the cricothyroid cartilage to provide a path for the tube.

The arcuately contoured tube 37 or 837 freely enters the slit and by virtue of the bulged lower tube end 38 or 838, is securely retained in the throat of the patient.

As is apparent, the assembly components, other than the marking strip and air tube, are then free to fall away from the neck of the patient, leaving only the air tube in place.

In the FIG. 1–5 embodiment, the pushing of the button 51 is a single action which, though producing release of first the knife and then the tube, appears to be almost a single operation, as in the FIG. 6–8 embodiment. It will be observed that the contour of the tube is such that the bulged end 38 or 838 thereof acts in the nature of a collar button to retain the tube in position pending the arrival of a doctor.

It is thus seen that a simple apparatus has been provided, enabling a lay user to rapidly provide an emergency breathing passage for a patient experiencing an upper respiratory obstruction, with the throat incising action not apparent to the user.

The above disclosure has been given by way of illustration and elucidation and not by way of limitation, and it is desired to protect all embodiments of the herein disclosed inventive concept within the scope of the appended claims.

What is claimed is:

1. Cricothyrotomy apparatus for establishing an emergency air breathing path for patients experiencing upper respiratory obstruction, said apparatus comprising: a housing; an air tube slideably mounted in said housing; a surgical blade in said housing; spring means biasing said air tube and said surgical blade to a position externally of said housing; detent means movably positioned to retain said surgical blade and said air tube against said spring biasing means; and means accessible from a point externally of said housing for releasing said detent means, to permit said biasing means to urge said surgical blade and said tube to a position externally of said housing.

2. Cricothyrotomy apparatus as in claim 1, having a marking strip formed with a notch contoured to fit against the lower edge of the adam's apple of a patient, and provided with means identifying the desired point of incision for insertion of the cricothyrotomy tube.

3. Cricothyrotomy apparatus as in claim 1 having guide means for guiding said tube during its movement by said tube biasing means.

4. Cricothyrotomy apparatus as in claim 2, in which said marking strip is provided with guide means, and said tube is formed with mating guide means, which, upon interengagement with said first name guide means, serve to orient the tube in desired position when it is released by said detent.

5. Cricothyrotomy apparatus as in claim 1 in which said air tube is formed with a flange at one end thereof slidably arranged within said housing, and a bulbous end on said tube opposite said flanged end, with an area of constriction in said tube between said flange and said bulbous end.

6. Cricothyrotomy apparatus as in claim 1, in which a flange is formed on said air tube, and said spring biasing means urging said tube out of said housing are arranged between said annular flange and said tube flange.

7. Cricothyrotomy apparatus as in claim 1 in which a sleeve is inserted in said housing surrounding said air tube and surgical blade; and said detent means comprise a detent bar pivoted on said sleeve within said housing.

8. Cricothyrotomy apparatus as in claim 1, in which said surgical blade is movable independently of said air tube; and said means for releasing said detent means act to release first said surgical blade and then said air tube.

9. Cricothyrotomy apparatus as in claim 8 in which said housing is provided with stop means limiting the movement of said surgical blade under the biasing action of said spring means.

10. Cricothyrotomy apparatus as in claim 8 in which an inner annular flange defining an opening through which said surgical blade may pass is formed in said housing; and a flange is formed on said surgical blade, said blade flange overlying said annular flange and butting against said annular flange when said detent releases said surgical blade, whereby the motion of said surgical blade is limited.

11. Cricothyrotomy apparatus as in claim 8, in which said spring means urging said surgical blade out of said housing, are arranged between said blade flange and an end wall of said housing.

12. Cricothyrotomy apparatus as in claim 8, in which a sleeve is inserted in said housing, and said detent means comprise a detent bar pivoted on a wall of said sleeve; a longer detent retaining said tube; a shorter detent retaining said knife; an actuating button extending through an opening in said housing pivoting said detent bar to release first said knife and then said tube.

13. Cricothyrotomy apparatus as in claim 1 in which said surgical blade is formed on the end of said tube first moving out of said housing.

14. A marking strip for identifying the point of incision when inserting a cricothyrotomy tube, said strip having a notch contoured to the shape of the bottom of the adam's apple; a marking indicia on the strip at a distance from the notch corresponding to the typical distance between the bottom of the adam's apple and the cricothyroid membrane.

15. A method of inserting a cricothyrotomy tube in a patient's throat in a fashion minimizing the awareness of the user of the procedure, said method comprising the steps of: enclosing a spring pressed cricothyrotomy tube from view in a manually holdable enclosure; enclosing a spring pressed knife blade in said enclosure; applying the enclosure containing the knife and tube to the throat of an asphyxiating patient; releasing the knife from the enclosure for movement from the end of the enclosure into the patient's throat; releasing the tube for movement from the end of the enclosure into the patient's throat through the slit formed by the knife; and thereafter removing the enclosure.

16. A method of rapidly identifying the point of incision for insertion of a cricothyrotomy tube in the neck of the patient, said method comprising the steps of forming a strip of material with a notch along one edge thereof; forming indicia on the strip at a distance from said notch equal to the typical distance between the bottom of the adam's apple and the area between the cricoid and thyroid cartilage; and applying the strip to the neck of a patient beneath the adam's apple with the notch of the strip underlying the adam's apple.

* * * * *